US006258573B1

(12) United States Patent
Suga et al.

(10) Patent No.: US 6,258,573 B1
(45) Date of Patent: *Jul. 10, 2001

(54) METHOD OF PRODUCING L-SERINE BY FERMENTATION

(75) Inventors: Mikiko Suga; Masakazu Sugimoto, both of Kawasaki; Tsuyoshi Osumi, Tokyo; Tsuyoshi Nakamatsu; Wataru Hibino, both of Kawasaki; Mika Ito, Yokkaichi, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/222,786

(22) Filed: Dec. 30, 1998

(30) Foreign Application Priority Data

Jan. 12, 1998 (JP) .................................. 10-003751
Dec. 11, 1998 (JP) .................................. 10-353513

(51) Int. Cl.⁷ ............................ C12P 13/06; C12P 13/04; C12N 1/20; C12N 9/04; C12N 15/00
(52) U.S. Cl. ................ 435/116; 435/252.3; 435/252.32; 435/190; 435/320.1; 435/106
(58) Field of Search ........................... 536/23.2; 435/190, 435/252.32, 252.1, 106, 108, 116

(56) References Cited

U.S. PATENT DOCUMENTS

| 5,407,824 | 4/1995 | Katsumata et al. | 435/252.3 |
| 5,447,857 | 9/1995 | Katsumata et al. | 435/108 |
| 5,618,716 | 4/1997 | Burlingame | 435/106 |
| 5,856,148 | 1/1999 | Burlingame | 435/106 |

FOREIGN PATENT DOCUMENTS

| 3-7591 | 1/1991 | (JP) . |
| 2584409 | 2/1997 | (JP) . |
| 10248588 | * 9/1998 | (JP) . |
| WO 93/12235 | 6/1993 | (WO) . |

* cited by examiner

Primary Examiner—Rebecca E. Prouty
(74) Attorney, Agent, or Firm—Oblon, Spivak, McClelland, Maier & Neustadt, P.C.

(57) ABSTRACT

Disclosed is a coryneform bacterium having resistance to azaserine or β-(2-thienyl)-DL-alanine and having L-serine productivity. Also, disclosed are D-3-phosphoglycerate dehydrogenase derived from a coryneform bacterium, in which feedback inhibition by L-serine is desensitized; the D-3-phosphoglycerate dehydrogenase, which is obtainable from a coryneform bacterium having resistance to azaserine or β-(2-thienyl)-DL-alanine and having L-serine productivity; the D-3-phosphoglycerate dehydrogenase having an amino acid sequence depicted in SEQ ID NO: 12 in Sequence Listing or the sequence including substitution, addition or deletion of one or more amino acids, wherein an amino acid residue corresponding to the 325th glutamic acid residue of the amino acid sequence in the SEQ ID NO: 12 is replaced with an amino acid other than glutamic acid; the D-3-phosphoglycerate dehydrogenase that has an amino acid sequence depicted in SEQ ID NO: 11 in Sequence Listing; a DNA coding for the D-3-phosphoglycerate dehydrogenase described above; the DNA that has a base sequence depicted in SEQ ID NO: 13 in Sequence Listing; a coryneform bacterium which harbors a recombinant DNA containing the DNA; and a method of producing L-serine, comprising the steps of cultivating the bacterium described above in a medium to allow accumulation of L-serine in the medium, and collecting the L-serine from the medium.

6 Claims, 2 Drawing Sheets

METHOD OF PRODUCING L-SERINE BY FERMENTATION

FIELD OF THE INVENTION

The present invention relates to a method of producing L-serine for use in the production of amino acid mixtures utilized in the field of pharmaceuticals, chemicals, and cosmetics, to coryneform bacteria constituting the method, to D-3-phosphoglycerate dehydrogenase (hereafter, sometimes referred to as "3-PGDH"), and to DNA coding for the 3-PGDH.

BACKGROUND OF THE INVENTION

As a conventional method of producing L-serine by fermentation, there has been reported the method in which a bacterial strain capable of converting glycine and sugar into L-serine is used in a medium containing 30 g/L of glycine to produce at most 14 g/L of L-serine. The conversion yield of glycine into L-serine by this method amounted to 46% (Kubota K. Agricultural Biological Chemistry, 49, 7–12 (1985)). Using a bacterial strain capable of converting glycine and methanol into L-serine, 53 g/L of L-serine can be produced from 100 g/L of glycine (T. Yoshida et al., Journal of Fermentation and Bioengineering, Vol. 79, No. 2, 181–183, 1995). In the method using a bacterium belonging to the genus Nocardia, it has been known that the L-serine productivity of the bacterium can be improved by breeding those strains resistant to serine hydroxamate, azaserine or the like (Japanese Patent Publication No. 57-1235). However, these methods involve use of glycine that is a precursor of L-serine and include complicated operation and is disadvantageous from the viewpoint of costs.

As strains that can ferment L-serine directly from a sugar and do not need addition of the precursor of L-serine to the medium, there has been known *Corynebacterium glutamicum* that is resistant to D-serine, α-methylserine, o-methylserine, isoserine, serine hydroxamate, and 3-chloroalanine but the accumulation of L-serine is as low as 0.8 g/L (Nogei Kagakukaishi, Vol. 48, No. 3, p201–208, 1974). Accordingly, a further strain improvements of are needed for direct fermentation of L-serine on an industrial scale.

On the other hand, regarding coryneform bacteria, there have been disclosed a vector plasmid that is capable of autonomous replication in the cell and having a drug resistance marker gene (cf. U.S. Pat. No. 4,514,502) and a method of introducing a gene into the cell (Japanese Patent Application Laid-open No. 2-207791), and the possibility of growing L-threonine or L-isoleucine producing bacteria (U.S. Pat. Nos. 4,452,890 and 4,442,208). Also, regarding the growth of L-lysine producing bacteria, there has been known a technology involving the incorporation of a gene participating in the biosynthesis of L-lysine into a vector plasmid and the amplification of the plasmid in the cell (Japanese Patent Application Laid-open No. 56-160997).

In the case of *Escherichia coli,* the enzymes participating in the biosynthesis of L-serine include an enzyme that is susceptible to feedback inhibition relative to L-serine production in the wild type and an example has been known in which the introduction of a mutant gene that has been mutated so that the feedback inhibition could be desensitized resulted in an enhancement in the L-serine (Japanese Patent No. 2584409). As such genes, there has been known specifically 3-PGDH gene (hereafter, the gene coding for 3-PGDH protein will also be referred to "serA").

Further, in the case of coryneform bacteria, an example has been known in which the amplification of 3-PGDH gene influences the productivity of L-tryptophane (Japanese Patent Application Laid-open No. 3-7591).

SUMMARY OF THE INVENTION

An object of the present invention is to provide a microorganism that converts a sugar into L-serine and to provide a method of accumulating L-serine in a culture medium utilizing the ability of the microorganism to convert the sugar into L-serine, i.e., a method of producing L-serine that is advantageous in practicing on an industrial scale.

As a result of intensive investigation on the method of producing L-serine with view to achieving the above object, it has now been discovered by the present inventors that screening a coryneform bacterium having L-serine productivity, particularly preferably a mutant strain exhibiting resistance to azaserine or β-(2-thienyl)-DL-alanine derived from a strain of the coryneform bacterium but is deficient in L-serine decomposing activity as a parent strain and conducting L-serine fermentation using the screened strain will enhance the accumulation of L-serine drastically. The present invention has been completed based on this discovery.

That is, the present invention relates to a coryneform bacterium having resistance to azaserine or β-(2-thienyl)-DL-alanine and having L-serine productivity.

Further, the present invention relates to D-3-phosphoglycerate dehydrogenase derived from a coryneform bacterium, in which feedback inhibition by L-serine is desensitized; to the D-3-phosphoglycerate dehydrogenase as described above, obtainable from a coryneform bacterium having resistance to azaserine or β-(2-thienyl)-DL-alanine and having L-serine productivity; to D-3-phosphoglycerate dehydrogenase having an amino acid sequence amino acid sequence depicted in SEQ ID NO: 12 in Sequence Listing or the sequence including substitution, addition or deletion of one or more amino acids, wherein an amino acid residue corresponding to the 325th glutamic acid residue of the amino acid sequence in the SEQ ID NO: 12 is replaced with an amino acid other than glutamic acid; and to the D-3-phosphoglycerate dehydrogenase as described above that has an depicted in SEQ ID NO: 14 in Sequence Listing.

Still further, the present invention relates to a DNA coding for the D-3-phosphoglycerate dehydrogenase described above and to the DNA described above having a base sequence as depicted in SEQ ID NO: 13 in Sequence Listing.

Yet further, the present invention relates to a coryneform bacterium that harbors a recombinant DNA containing the DNA described above.

Further, the present invention relates to a method of producing L-serine, comprising the steps of cultivating the bacterium as described above in a medium to allow accumulation of L-serine in the medium, and collecting the L-serine from the medium.

Specific examples of the coryneform bacterium having resistance to azaserine or β-(2-thienyl)-DL-alanine and having L-serine productivity include *Brevibacterium flavum* AJ13324 and AJ13327 or *Brevibacterium flavum* AJ13325.

The present invention provides coryneform bacteria that produce L-serine from a sugar. The coryneform bacteria can be utilized in a method of producing L-serine that is industrially advantageous.

DETAILED DESCRIPTION OF THE INVENTION

Figure 1:
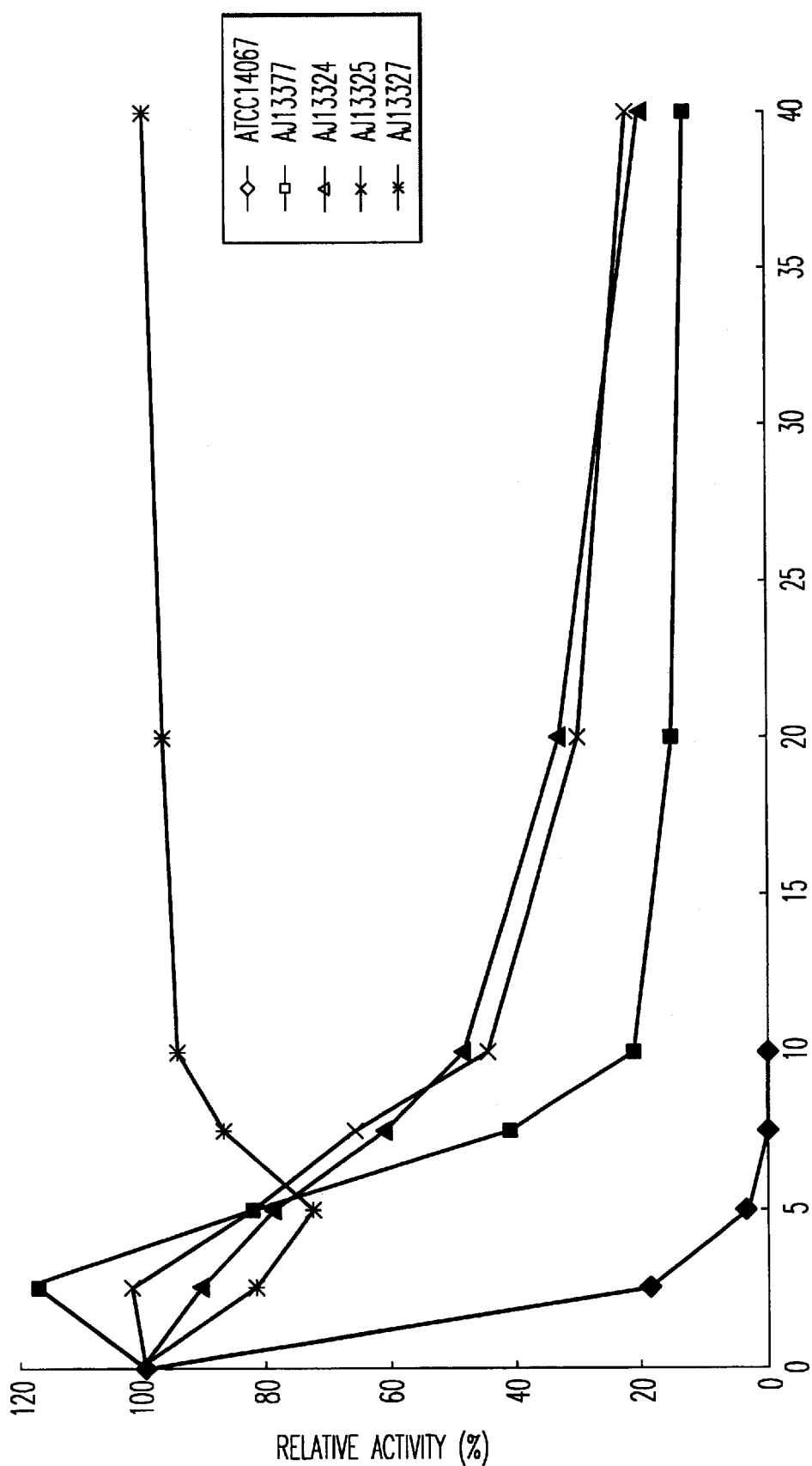
FIG. 1 illustrates a manner of feedback inhibition of 3-PGDH derived from various strains by L-serine. The horizontal axis indicates the concentration of L-serine in the enzyme solution. The vertical axis indicates percentage of the 3-PGDH activity in the presence of L-serine to that in the absence of L-serine. Symbol ♦ illustrates a manner of feedback inhibition of 3-PGDH derived from ATCC14067 strain by L-serine. Symbol ■ illustrates a manner of feedback inhibition of 3-PGDH derived from AJ13377 strain by L-serine. Symbol ▲ illustrates a manner of feedback inhibition of 3-PGDH derived from AJ13324 strain by L-serine. Symbol x illustrates a manner of feedback inhibition of 3-PGDH derived from AJ13325 strain by L-serine. Symbol ★ illustrates a manner of feedback inhibition of 3-PGDH derived from AJ13327 strain by L-serine.

The coryneform bacteria referred to in the present invention are a group of microorganisms as defined in *Bergey's Manual of Determinative Bacteriology*, 8th ed., p. 599 (1974), which are aerobic Gram-positive rods having no acid resistance and no spore-forming ability. The coryneform bacteria include bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium and bacteria belonging to the genus Microbacterium.

The coryneform bacteria of the present invention that have resistance to azaserine or β-(2-thienyl)-DL-alanine and having L-serine productivity, preferably those strains of these coryneform bacteria that are deficient in L-serine decomposing activity, are artificially mutated or induced from wild type or L-serine producing coryneform bacteria as a parent strain.

The coryneform bacteria that have resistance to azaserine or β-(2-thienyl)-DL-alanine, which are deficient in L-serine decomposing activity and have L-serine productivity can be obtained, for example, as follows. That is, *Brevibacterium flavum* ATCC 14067 is subjected to mutation treatment by a conventional method (contact with N-methyl-N'-nitro-N-nitroso-guanidine or the like) to obtain a mutant strain deficient in L-serine decomposing activity and using this strain as a parent strain, strains resistant to azaserine or β-(2-thienyl)-DL-alanine are obtained. From among the mutant strains obtained by the method as described above can be obtained strains that accumulate L-serine in high concentrations.

The strains resistant to azaserine or β-(2-thienyl)-DL-alanine can also be obtained by introducing the mutant serA described below into parent strains or mutant strains deficient in L-serine decomposing activity.

The term "azaserine resistance" refers to the property that a bacterium grows faster than the wild type in a medium containing azaserine. For example, those strains that form colonies on a solid medium containing 0.25 g/L of azaserine at 30° C. within 4 to 5 days are said to have azaserine resistance.

Similarly, the term "β-(2-thienyl)-DL-alanine resistance" refers to the property that a bacterium grows faster than the wild type in a medium containing β-(2-thienyl)-DL-alanine. For example, those strains that form colonies on a solid medium containing 0.25 g/L of β-(2-thienyl)-DL-alanine at 30° C. within 4 to 5 days are said to have β-(2-thienyl)-DL-alanine resistance.

3-PGDH catalyzes reaction in which 3-phosphoglycerate is oxidized into 3-phosphohydroxylpyruvic acid in the presence of nicotinamide adenine dinucleotide (NAD) as a coenzyme.

The activity of 3-PGDH can be determined, for example, by the measurement of a decrease in coenzyme $NADH_2$ in a reverse reaction (E. Sugimoto and L. I. Pizer, JBC, 243, 2081, 1968) or synthesis of coenzyme $NADH_2$ in a forward reaction (Salach H. J. Method in Enzymology, vol.9, 216–220, 1966) by absorbance at 340 nm.

3-PGDH can be purified by collecting cells from the culture broth of a coryneform bacterium, fragmenting the collected cells by sonication and subsequent ultracentrifugation, and isolating the targeted enzyme from the supernatant by a conventional method. More particularly, 3-PGDH can be purified by sequentially concentrating fractions having 3-PGDH activity by precipitation with ammonium sulfate, gel filtration, cation exchange resin chromatography, anion exchange resin chromatography, reverse phase chromatography and the like.

3-PGDH derived from a wild type coryneform bacterium is susceptible to feedback inhibition by L-serine and its activity is almost completely inhibited in the presence of 10 mM of L-serine. By the term "3-PGDH in which feedback inhibition by L-serine is desensitized" is meant 3-PGDH having 20% or more, preferably 40% or more, more preferably 90% or more of the activity in the absence of L-serine even in the presence of 10 mM of L-serine. 3-PGDH derived from *Brevibacterium flavum* AJ13327 described in the examples hereinbelow retains substantially 100% of the activity in the presence of 80 mM of L-serine and therefore one of the most preferred 3-PGDHs.

3-PGDH derived from a wild type coryneform bacterium (hereafter, DNA coding for this is also referred to as "wild type sera") has the amino acid sequence depicted in SEQ ID NO : 12 in Sequence Listing. Specific examples of the 3-PGDH in which feedback inhibition by L-serine is desensitized (hereafter, DNA coding for this is also referred to as "mutant serA") include D-3-phosphoglycerate dehydrogenase characterized in that in D-3-phosphoglycerate dehydrogenase having the amino acid sequence depicted in SEQ ID NO: 12 in Sequence Listing or the same amino acid sequence as above but has substitution, addition or deletion of one or more amino acids, the amino acid residue corresponding to the 325th glutamic acid residue of the amino acid sequence in the SEQ ID NO: 12 has been substituted by other amino acid. Most preferred as the other amino acid residue is a lysine residue.

The DNA fragment containing serA gene from a coryneform bacterium can be isolated, for example, by preparing chromosomal DNA according to the method of Saito and Miura (H. Saito and K. Miura, Biochem. Biophys. Acta, 72, 619 (1963)) or the like and then amplifying serA gene by polymerase chain reaction method (PCR: polymerase chain reaction; cf. White, T. J. et al.; Trends Genet. 5, 185 (1989)). For example, in order to amplify DNA fragment containing ORF (172 to 1705) of SEQ ID NO: 11 in Sequence Listing, any 20 to 30 bases are selected from the region from the first base in SEQ ID NO: 11 to the base immediately before ATG to obtain one primer. Further, any 20 to 30 bases are selected from the region from the base immediately after the termination codon to the last base in SEQ ID NO: 11 to obtain another primer.

When serA is isolated from a wild type strain of 3-PGDH, wild type serA is obtained and isolation of serA from a mutant harboring 3-PGDH in which feedback inhibition by L-serine is desensitized (3-PGDH mutant) gives mutant serA. Specifically, the wild type serA has the sequence depicted in SEQ ID NO: 11 in Sequence Listing, and mutant serA has the sequence depicted in SEQ ID NO: 13 in Sequence Listing.

It is preferred that serA amplified by PCR method is ligated with vector DNA autonomously replicable in cells of Escherichia coli and/or coryneform bacteria to prepare recombinant DNA, and the recombinant DNA is introduced into cells of Escherichia coli beforehand. Such provision makes following operations easy. The vector autonomously replicable in cells of Escherichia coli is preferably a plasmid vector which is preferably autonomously replicable in cells of a host, including, for example, pUC19, pUC18, pBR322, pHSG299, pHSG399, pHSG398, and RSF1010.

Recombinant DNA may be prepared by utilizing transposon (WO 02/02627 International Publication Pamphlet, WO 93/18151 International Publication Pamphlet, European Patent Application Laid-open No. 0445385, Japanese Patent Application Laid-open No. 6-46867, Vertes, A. A. et al., Mol. Microbiol., 11, 739–746 (1994), Bonamy, C., et al., Mol. Microbiol., 14, 571–581 (1994), Vertes, A. A. et al., Mol. Gen. Genet., 245, 397–405 (1994), Jagar, W. et al., FEMS Microbiology Letters, 126, 1–6 (1995), Japanese Patent Application Laid-open No. 7-107976, Japanese Patent Application Laid-open No. 7-327680, etc.), phage vectors, recombination of chromosomes (Experiments in Molecular Genetics, Cold Spring Harbor Laboratory Press (1972); Matsuyama, S. and Mizushima, S., J. Bacteriol., 162, 1196 (1985)) and the like.

When a DNA fragment having an ability to allow a plasmid to be autonomously replicable in coryneform, bacteria is inserted into these vectors, they can be used as a so-called shuttle vector autonomously replicable in both Escherichia coli and coryneform bacteria.

Such a shuttle vector includes the followings. Microorganisms harboring each of vectors and deposition numbers in international deposition facilities are shown in parentheses.

pHC4: Escherichia coli AJ12617 (FERM BP-3532)
pAJ655: Escherichia coli AJ11882 (FERM BP-136)
   Corynebacterium glutamicum SR8201 (ATCC 39135)
pAJ1844: Escherichia coli AJ11883 (FERM BP-137)
   Corynebacterium glutamicum SR8202 (ATCC 39136)
pAJ611: Escherichia coli AJ11884 (FERM BP-138)
pAJ3148: Corynebacterium glutamicum SR8203 (ATCC 39137)
pAJ440: Bacillus subtilis AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000×g to obtain a supernatant to which polyethylene glycol is added, followed by fractionation and purification by means of cesium chloride-ethidium bromide equilibrium density gradient centrifugation.

Escherichia coli can be transformed by introducing a plasmid in accordance with, for example, a method of D. M. Morrison (Methods in Enzymology, 68, 326 (1979)) or a method in which recipient cells are treated with calcium chloride to increase permeability for DNA (Mandel, M. and Higa, A., J. Mol. Biol., 53, 159 (1970)).

Introduction of plasmids to coryneform bacteria to cause transformation can be performed by the electric pulse method (Sugimoto et al., Japanese Patent Application Laid-open No. 2-207791).

Examples of the coryneform bacterium used to introduce the DNA described above include, for example, the following wild type strains:
Corynebacterium acetoacidophilum ATCC 13870;
Corynebacterium acetoglutamicum ATCC 15806;
Corynebacterium callunae ATCC 15991;
Corynebacterium glutamicum ATCC 13032;
(Brevibacterium divaricatum) ATCC 14020;
(Brevibacterium lactofermentum) ATCC 13869;
(Corynebacterium lilium) ATCC 15990;
(Brevibacterium flavum) ATCC 14067;
Corynebacterium melassecola ATCC 17965;
Brevibacterium saccharolyticum ATCC 14066;
Brevibacterium immariophilum ATCC 14068;
Brevibacterium roseum ATCC 13825;
Brevibacterium thiogenitalis ATCC 19240;
Microbacterium ammoniaphilum ATCC 15354;
Corynebacterium thermoaminogenes AJ12340 (FERM BP-1539).

The transformed strains obtained by introduction of recombinant DNA containing the mutant serA into the coryneform bacterial as described above produces 3-PGDH in which feedback inhibition by L-serine is desensitized. The transformed strains have resistance to azaserine or β-(2-thienyl)-DL-alanine.

For L-serine production using the strain of the present invention, the following methods may be used. As the medium to be used, there can be used conventional liquid mediums containing carbon sources, nitrogen sources, inorganic salts, and optionally organic trace nutrients such as amino acids, vitamins, etc., if desired.

As carbon sources, it is possible to use sugars such as glucose, sucrose, fructose, galactose; saccharified starch solutions, sweet potato molasses, sugar beet molasses and hightest molasses which are including the sugars described above; organic acids such as acetic acid; alcohols such as ethanol; glycerol and the like.

As nitrogen sources, it is possible to use ammonia gas, aqueous ammonia, ammonium salts, urea, nitrates and the like. Further, organic nitrogen sources for supplemental use, for example, oil cakes, soybean hydrolysate liquids, decomposed casein, other amino acids, corn steep liquor, yeast or yeast extract, peptides such as peptone, and the like, may be used.

As inorganic ions, phosphoric ion, magnesium ion, calcium ion, iron ion, manganese ion and the like may be added optionally.

In case of using the microorganism of the present invention which requires nutrients such as amino acids for its growth, the required nutrients should be supplemented.

The microorganisms are incubated usually under aerobic conditions at pH 5 to 8 and temperature ranges of 25 to 40° C. The pH of the culture medium is controlled at a predetermined value within the above-described ranges depending on the presence or absence of inorganic or organic acids, alkaline substances, urea, calcium carbonate, ammonia gas, and the like.

L-Serine can be collected from the fermentation liquid, for example, by separating and removing the cells, subjecting to ion exchange resin treatment, concentration cooling crystallization, membrane separation, and other known methods in any suitable combination. In order to remove impurities, activated carbon adsorption and recrystallization may be used for purification.

DESCRIPTION OF PREFERRED EMBODIMENTS

EXAMPLE 1

Construction of novel L-serine producing bacteria Brevibacterium flavum AJ13324 and AJ13327

*Brevibacterium flavum* AJ13324 and AJ13327 were constructed from *Brevibacterium flavum* AJ13377 that is deficient in L-serine decomposing activity obtained from wild type strain *Brevibacterium flavum* ATCC 14067.

To obtain a mutant, cells proliferated for 24 hours in a bouillon medium (a medium containing 1 g of fish meat extract, 1 g of polypeptone, 0.5 g of yeast extract, and 0.5 g of sodium chloride in 1 liter of water, adjusted to pH 7.0) were suspended in 100 mM phosphate buffer (pH 7.0) (containing $10^9$ to $10^{10}$ cells/ml). NG (N-methyl-N'-nitro-N-nitrosoguanidine) was added to the suspension to a concentration of 200 µg/ml and left to stand at 30° C. for 30 minutes. The thus NG treated cells were washed well with the above-described buffer.

To select strains having no L-serine decomposing activity from the NG treated cells, NG treated cells of *Brevibacterium flavum* ATCC 14067 after washed were spread on a bouillon agar medium and incubated at 30° C. for 24 hours to allow colony formation. Then, the colonies on the bouillon agar medium were used as a negative and replica formation was performed on a minimal medium and a minimal medium for selection. Then, strains were screened that grow on the minimal medium but do not grow on the minimal medium for selection. The minimal medium was a medium that contained 20 g of glucose, 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetra- to pentahydrate, 50 µg of biotin, 200 µg of thiamin hydrochloride, 200 µg of nicotinic acid amide, and 2.0 g of agar per liter of distilled water. The minimal medium for selection was a medium that contained 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetra- to pentahydrate, 50 µg of biotin, 200 µg of thiamin hydrochloride, 200 µg of nicotinic acid amide, 0.5 g of L-serine and 2.0 g of agar per liter of distilled water. Among the mutants obtained by this method were found many strains that have no L-serine decomposing activity and *Brevibacterium flavum* AJ13377 was obtained as one of such strains.

To select azaserine resistant strains from NG treated strains using *Brevibacterium flavum* AJ13377 as a parent strain, NG treated *Brevibacterium flavum* AJ13377 cells after washed were inoculated on a minimal medium for selection. The minimal medium for selection was a medium that contained 20 g of glucose, 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetra- to pentahydrate, 50 µg of biotin, 200 µg of thiamin hydrochloride, 200 µg of nicotinic acid amide, and 250 mg of azaserine per liter of distilled water. The NG treated mutant was incubated in the above-described medium at 30° C. for 5 to 10 days. The cell culture thus obtained was spread on a bouillon agar medium and incubated at 30° C. for 24 hours for colony formation. Azaserine resistant strains were obtained from the strains that formed colonies. The mutants thus obtained included many strains that accumulated L-serine in considerable amounts at high yields. From the strains were obtained two strains, i.e., *Brevibacterium flavum* AJ13324 and AJ13327. It was confirmed that these strains were able to grow in the presence of 0.25 g/L of azaserine.

EXAMPLE 2
Construction of novel L-serine producing bacterium *Brevibacterium flavum* AJ13325

*Brevibacterium flavum* AJ13325 was constructed from *Brevibacterium flavum* AJ13377 lacking L-serine. decomposing activity, which was obtained from the wild type strain *Brevibacterium flavum* ATCC 14067.

To select β-(2-thienyl)-DL-alanine resistant strains from NG treated strains using *Brevibacterium flavum* AJ13377 as a parent strain, *Brevibacterium flavum* AJ13377 cells were NG treated and washed before their inoculation on a minimal medium for selection. The minimal medium for selection was a medium that contained 20 g of glucose, 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetra- to pentahydrate, 50 µg of biotin, 200 µg of thiamin hydrochloride, 200 µg of nicotinic acid amide, and 250 mg of β-(2-thienyl)-DL-alanine per liter of distilled water. The NG treated mutant was incubated in the above-described medium at 30° C. for 5 to 10 days. The cell culture thus obtained was spread on a bouillon agar medium and incubated at 30° C. for 24 hours for colony formation. β-(2-Thienyl)-DL-alanine resistant strains were obtained from the strains that formed colonies. The mutants thus obtained included many strains that accumulated L-serine in considerable amounts at high yields. *Brevibacterium flavum* AJ13325 was obtained as one of such strains. It was confirmed that these strains were able to grow in the presence of 0.25 g/L of β-(2-thienyl)-DL-alanine.

EXAMPLE 3
Production of L-serine by novel L-serine producing bacteria *Brevibacterium flavum* AJ13324, AJ13325 and AJ13327

*Brevibacterium flavum* AJ13324, AJ13325 and AJ13327 were each incubated on a bouillon agar medium at 30° C. for 24 hours and a loopful of each microorganism was inoculated in a 500 ml shaking flask containing 20 ml of a fermentation medium having the composition shown in Table 1. As a control, the parent strains *Brevibacterium flavum* ATCC 14067 and AJ13377 were inoculated as a same manner as described above. The medium was adjusted to pH 7.0 with potassium hydroxide and autoclaved at 115° C. for 15 minutes. After the sterilization and cooling, calcium carbonate that had been dry air sterilized at 180° C. for 3 hours was added in an amount of 5 g/L.

TABLE 1

| Component | Content/liter |
| --- | --- |
| Glucose | 110.0 g |
| Potassium dihydrogen phosphate | 0.4 g |
| Magnesium sulfate heptahydrate | 0.4 g |
| Iron (II) sulfate heptahydrate | 0.01 g |
| Manganese sulfate tetra- to penta-hydrate | 0.01 g |
| Ammonium sulfate | 25.0 g |
| Thiamin hydrochloride | 100 µg |
| Biotin | 100 µg |
| Soy bean protein hydrochloric acid hydrolysate ("Mieki" (registered trademark) | 40 ml |
| pH | 7.0 |

Determination of L-serine using high performance liquid chromatography (Hitachi L-8500 Amino Acid Autoanalyzer) revealed that *Brevibacterium flavum* AJ13324, AJ13325 and AJ13327 accumulated L-serine in the medium in amounts of 15.2 g/L, 14.3 g/L, and 15.4 g/L, respectively. On the other hand, *Brevibacterium flavum* strains ATCC 14067 and AJ13377 incubated as a control accumulated L-serine in amounts of 0 g/L and 5.0 g/L, respectively.

The culture broth of *Brevibacterium flavum* AJ13324 was centrifuged and the supernatant was subjected to desalting treatment using cation exchange resin, followed by chromatographic separation with cation exchange resin and anion exchange resin to remove byproducts and purification by crystallization to obtain L-serine crystals of at least 99% purity at a yield from broth of 55%.

EXAMPLE 4
Measurement of 3-PGDH activity

*Brevibacterium flavum* AJ13324, AJ13325 and AJ13327 were each incubated on a bouillon agar medium at 30° C. for 24 hours and a loopful of each microorganism was inoculated in a 500 ml shaking flask containing 50 ml of a fermentation medium having the composition shown in Table 2. As a control, the parent strains *Brevibacterium flavum* ATCC 14067 and AJ13377 were inoculated as a same manner as described above. The medium for inoculation was adjusted to pH 5.5 with sodium hydroxide and autoclaved at 115° C. for minutes.

TABLE 2

| Component | Content/liter |
| --- | --- |
| Glucose | 30.0 g |
| Potassium dihydrogen phosphate | 1.0 g |
| Magnesium sulfate heptahydrate | 0.4 g |
| Iron (II) sulfate heptahydrate | 0.01 g |
| Manganese sulfate tetra- to penta-hydrate | 0.01 g |
| Ammonium sulfate | 3.0 g |
| Soy bean protein hydrochloric acid hydrolysate ("Mieki" (reqistered trademark) | 3.0 ml |
| Thiamin hydrochloride | 200 μg |
| Biotin | 50 μg |
| Urea | 3.0 g |
| Yeast extract | 2.0 g |
| pH | 5.5 |

After collecting cells from the culture broth of each strain, the cells were washed twice with physiological saline and suspended in 50 mM sodium phosphate buffer (pH 7.0) containing 2 mM dithiothreitol. After ice cooling, the suspension was subjected to a sonicator to fragment the cells and the resulting liquid was ultracentrifuged. The ultracentrifugaton was run at 45,000 rpm for 1 hour to obtain a crude enzyme solution.

The enzyme activity of 3-PGDH was measured by the method of Salach H. J. et al. (Method in Enzymology, vol 9, 216–220 (1966)).

More specifically, 0.4 ml of 0.015M NAD, 0.12 ml of 0.25M EDTA (pH 9, NaOH), 0.1 ml of 0.05M glutathione (pH 6, KOH), 0.5 ml of 1M hydrazine (pH 9, acetate), 0.6 ml of 1M Tris (pH 9, HCl), a suitable concentration of L-serine (0 to 40 mM), and water to make 2.3 ml, warmed to 25° C. in advance, were added. Then, 0.2 ml of the crude enzyme solution was added and the temperature was kept the same for 5 minutes. Thereafter, 0.5 ml of 0.1M 3-PGA (3-phosphoglycerate disodium salt, pH 7, NaOH) was added. After stirring, the absorbance at 340 nm of the reaction mixture was measured for 30 seconds. The reaction was carried out at 25° C.

For the measurement of activity, Hitachi U-2000A spectrophotometer was used.

FIG. 1 illustrates the results obtained. AJ13377 strain was relieved of L-serine sensitivity as compared with the wild type strain ATCC 14067. The AJ13324 strain was more relieved of L-serine sensitivity and the AJ13325 strain was of the same level as the AJ13324 strain in this respect. The AJ13327 strain was relieved of L-serine sensitivity greatly. And the inhibition was completely desensitized even in the presence of 80 mM L-serine.

Although some examples of desensitization of the inhibition of 3-PGDH by L-serine were reported on *Escherichia coli* (Tosa and Pizer, J. Bacteriol. 106: 972–982 (1971) or Japanese Patent Application Laid-open No. 6-510911), there has been known no example of complete desensitization of the inhibition in the presence of such a high concentration of L-serine.

EXAMPLE 5
Cloning of coryneform bacteria-derived wild type and mutant serA

As shown in Example 4, the feedback inhibition by L-serine was completely desensitized in the AJ13327 strain. Accordingly, cloning of serA gene coding for wild type 3-PGDH derived from the ATCC 14067 strain and mutant 3-PGDH derived from the AJ13327 strain was attempted in order to elucidate what the variation was like and confirm the amplification effect of 3-PGDH.

To amplify serA from the chromosome of *Brevibacterium flavum* using a PCR method, it is necessary to make a corresponding primer. Since no report has been made on the cloning and nucleotide sequence of serA of *Brevibacterium flavum*, the sequence of serA derived from Corynebacterium was used. Plasmid pDTS9901 was extracted from the strain *Corynebacterium glutamicum* K82 (cf. FERM BP-2444 and Japanese Patent Application Laid-open No. 3-7591) in which the serA fragment derived from Corynebacterium was cloned using Wizard Minipreps DNA Purification System (manufactured by Promega) and a DNA fragment of about 1.4 kb containing serA was cleaved with restriction enzyme BamHI (manufactured by Takara Shuzo Co., Ltd.).

Figure 2:
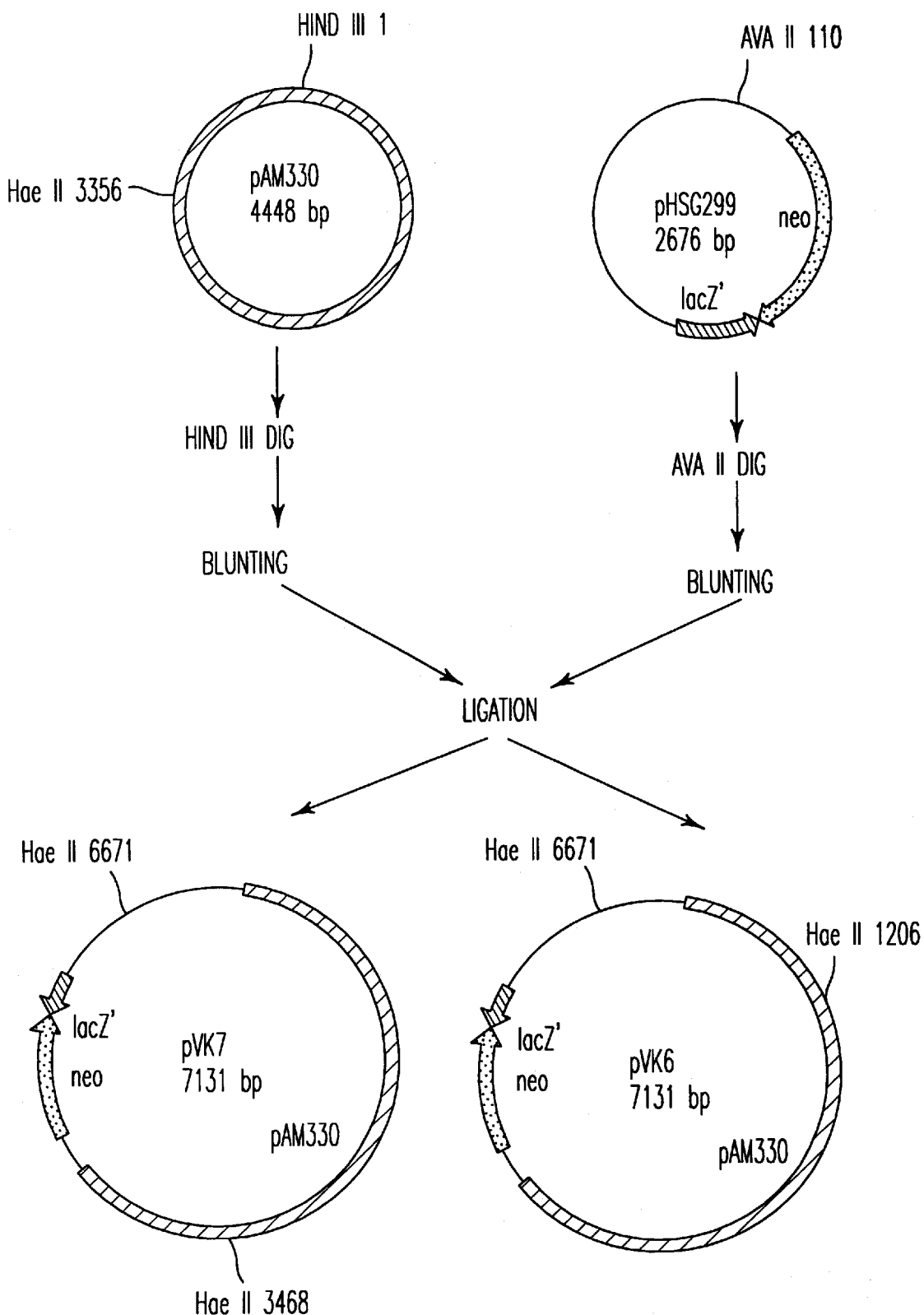
FIG. 2 illustrates the construction of plasmids pVK7 and pVK6.

As a vector for cloning the gene fragment, there was used a newly constructed cloning vector pVK7 for coryneform bacteria.

pVK7 was constructed by ligating (a cloning vector for *Escherichia coli*) pHSG299 (Kmr; Takeshita, S. et al., Gene, 61, 63–74 (1987), Japanese Patent Application Laid-open No. 10-215883), to pAM330, a cryptic plasmid of *Brevibacterium lactofermentum,* in the manner described below. pHSG299 was cleaved with monospecific restriction enzyme AvaII (manufactured by Takara Shuzo Co., Ltd.) and blunt ended with T4 DNA polymerase. This was ligated with pAM330 that had been cleaved with HindIII (manufactured by Takara Shuzo Co., Ltd.) and blunt ended with T4 DNA polymerase. The two types of plasmids obtained were designated pVK6 and pVK7 depending on the direction of pAM330 insertion relative to pHSG299, and pVK7 was used in the following experiments. pVK7 was capable of autonomous replication in *Escherichia coli* and *Brevibacterium lactofermentum* and retains the multiple cloning site and lacZ' derived from pHSG299. FIG. 2 illustrates the process of constructing pVK6 and pVK7.

To the shuttle vector pVK7 thus constructed was ligated a DNA fragment of about 1.4 kb containing serA. pDTS9901 was cleaved with restriction enzyme BamHI (manufactured by Takara Shuzo Co., Ltd.) and ligated to pVK7 also cleaved with restriction enzyme BamHI. The ligation of DNA was performed using DNA Ligation Kit (manufactured by Takara Shuzo Co., Ltd.) according to the prescribed method.

For the sequencing reaction, use was made of PCR thermal cycler MP type (manufactured by Takara Shuzo Co., Ltd.) and of Dye Terminator Cycle Sequencing FS Ready Reaction Kit (manufactured by Perkin Elmer). As the DNA primer, there were used M13(−21), RV primer (manufactured by Takara Shuzo Co., Ltd.). The SEQ ID NO: 1 in Sequence Listing shows the sequence thus obtained. SEQ ID NO: 2 shows an amino acid sequence that can be coded for by this sequence.

A primer was synthesized based on the base sequence thus determined and serA was amplified by a PCR method using the chromosomal DNA of the mutant *Brevibacterium flavum* AJ13327 as a template. The SEQ ID NOS: 3 and 4 in Sequence Listing show the N-terminal side and C terminal side sequences, respectively, of the DNA primer that were synthesized for gene amplification.

In the preparation of the chromosomal DNA of *Brevibacterium flavum*, use is made of Genomic DNA Purification Kit (Bacterial) (manufactured by Advanced Genetic Technologies Corp.) and the preparation method was according to the annexed protocol.

For the PCR reaction, use is made of PCR Thermal Cycler MP type (Takara Shuzo Co., Ltd.) and of TaKaRa Taq (manufactured by Takara Shuzo Co., Ltd.).

The PCR product was ligated directly to plasmid pCR2.1 vector using Original TA Cloning Kit (manufactured by Invitrogen) and transformation was performed using competent cell of INVαF'. The transformed cells were spread on L medium (10 g/L of bactotryptone, 5 g/L of bactoyeast extract, 15 g/L of NaCl, and 15 g/L of agar) further containing 40 μg/ml of X-Gal (5-bromo-4-chloro-3-indolyl-β-D-galactoside) and 25 μg/ml of Kanamycin, and incubated overnight. The white colonies, which appeared, were collected and separated to single colonies to obtain a transformed strain.

Plasmids were extracted from the transformed strain and those plasmids of which insertion of the serA fragment was confirmed by a PCR method were treated with restriction enzyme EcoRI and ligated to the shuttle vector pVK. Determination of the base sequence of the product suggested that no full-length sequence be contained on the C-terminal side. The sequence thus obtained corresponds to the region from 277 bases upstream of SEQ ID NO: 13 on the 5' side to the 1134th base of SEQ ID NO: 13 in Sequence Listing on the 3' side.

To obtain a fragment containing the full length serA gene, cloning of a deleted part from the chromosomal DNA of *Brevibacterium flavum* AJ13327 strain was performed according to the annexed protocol using TaKaRa LA PCR in vitro Cloning Kit (manufactured by Takara Shuzo Co., Ltd.)

First, the chromosomal DNA thus prepared was completely digested with various restriction enzymes and ligated with cassettes having respective restriction enzyme sites corresponding thereto. Cassette primer (C1) (SEQ ID NO: 5 in Sequence Listing) and a primer complementary to a known region of DNA (S1) (SEQ ID NO: 6 in Sequence Listing) were used for carrying out first PCR. Using a portion of the reaction mixture, second PCR was carried out with inner primer C2 (SEQ ID NO: 7 in Sequence Listing) and S2 (SEQ ID NO: 8 in Sequence Listing) to amplify only the targeted DNA.

When EcoRI (manufactured by Takara Shuzo Co., Ltd.) was used as the restriction enzyme, the amplification of the targeted DNA was confirmed and the base sequence of the PCR product was determined directly. Based on the base sequence thus obtained, a primer coding for the C-terminal side was made and the fragments containing full length serA were collected from *Brevibacterium flavum* ATCC 14067 as a wild type strain and *Brevibacterium flavum* AJ13327 as a mutant strain. SEQ ID NOS: 9 and 10 in Sequence Listing show the sequences of N-terminal and C-terminal side DNA primers, respectively.

The gene fragments containing wild type serA and mutant serA, respectively, in their full length were ligated to EcoRI-cleaved shuttle vector pVK7 using original TA Cloning Kit (manufactured by Invitrogen). Plasmids harboring respective gene fragments were made separately and their base sequence was determined. SEQ ID NOS: 11 and 13 indicate the sequences of the wild type and of mutant, respectively. SEQ ID NOS: 12 and 14 indicate amino acid sequences that these sequences can code for. Comparing the base sequences thus determined, it was confirmed that in the mutant serA, the 1087th base, G, was mutated into A and as a result, the 325th amino acid, glutamic acid, was changed to lysine.

EXAMPLE 6

Introduction of Plasmid Containing 3-PGDH Gene into *Brevibacterium flavum*

Plasmids harboring wild type serA or mutant serA were each introduced into *Brevibacterium flavum* AJ13377. The plasmids were introduced by the electric pulse method (Sugimoto et al., Japanese Patent Application Laid-open No. 2-207791). Transformed cells were selected in a complete medium containing 25 μg/ml of kanamycin.

EXAMPLE 7

Production of L-serine by Transformed Cells

Transformed cells each having introduced therein plasmids harboring gene fragments containing wild serA or mutant serA in their full-length were incubated in a 500 ml shaking flask according to Example 3, and L-serine produced was determined. As a control, the AJ13377 strain as a host was incubated similarly.

In the transformed cell having introduced therein the wild type serA was observed no influence on its L-serine productivity whereas in the transformed cell having introduced therein the mutant serA was confirmed an increase in L-serine productivity (Table 3).

TABLE 3

| Strain | Amplified Gene | Amount of L-serine that accumulated (g/L) |
| --- | --- | --- |
| AJ13377 | — | 5.0 |
|  | serA | 5.0 |
|  | serA* | 12.0 | serA*: Mutant serA gene

*Brevibacterium flavum* AJ13377 has been deposited since Oct. 15, 1997 in National Institute of Bioscience and Human Technology of Agency of Industrial Science and Technology of Ministry of International Trade and Industry (zip code: 305-8566, 1-3 Higashi 1-Chome, Tsukuba-shi, Ibaraki-ken, Japan), as accession number of FERM P-16471, and transferred from the original deposition to international deposition based on Budapest Treaty on Nov. 20, 1998, and has been deposited as accession number of FERM BP-6576.

Further, the plasmid containing the mutant serA was harbored in *Brevibacterium flavum* ATCC 14067. The plasmid-harboring strain has been awarded *Brevibacterium flavum* AJ13378 and deposited since Oct. 15, 1997 in National Institute of Bioscience and Human Technology of Agency of Industrial Science and Technology of Ministry of International Trade and Industry (zip code: 305-8566, 1-3 Higashi 1-Chome, Tsukuba-shi, Ibaraki-ken, Japan), as accession number of FERM P-16472, and transferred from the original deposition to international deposition based on Budapest Treaty on Nov. 20, 1998, and has been deposited as accession number of FERM BP-6577.

What is claimed is:

1. An isolated D-3-phosphoglycerate dehydrogenase obtainable from coryneform bacterium having an amino acid sequence depicted in SEQ ID NO: 12 in the Sequence Listing or said sequence including substitution, addition or deletion of one or more amino acids, wherein an amino acid residue corresponding to the 325th glutamic acid residue of the amino acid sequence in the SEQ ID NO: 12 is replaced with an amino acid other than glutamic acid.

2. An isolated D-3-phosphoglycerate dehydrogenase, which has an amino acid sequence depicted in SEQ ID NO: 14 in Sequence Listing.

3. A DNA coding for the D-3-phosphoglycerate dehydrogenase as claimed in claim 1 or claim 2.

4. The DNA as claimed in claim 3, wherein said DNA has a base sequence depicted in SEQ ID NO:13 in the Sequence Listing.

5. A coryneform bacterium which harbors a recombinant DNA containing the DNA as claimed in claim 3.

6. A method of producing L-serine, comprising the steps of cultivating the bacterium as claimed in claim 5 in a medium to allow accumulation of L-serine in the medium, and collecting the L-serine from the medium.

* * * * *

SEQUENCE LISTING

<160> NUMBER OF SEQ ID NOS: 14

<210> SEQ ID NO 1
<211> LENGTH: 1432
<212> TYPE: DNA
<213> ORGANISM: Corynebacterium glutamicum
<220> FEATURE:
<221> NAME/KEY: CDS
<222> LOCATION: (398)..(1432)

<400> SEQUENCE: 1

```
ggatccggac acacgtgaca aaattgtaga aaattggatg attttgtcac gcctgtctgg      60
tttagctctg gttcgggacg ggcgtggaat ggaggtagcg caccgagacc ttgacccgcg     120
gcccgacaag ccaaaagtcc ccaaaacaaa cccacctcgc cggagacgtg aataaaattc     180
gcagctcatt ccatcagcgt aaacgcagct ttttgcatgg tgagacacct ttgggggtaa     240
atctcacagc atgaatctct gggttagatg actttctggg tgggggaggg tttagaatgt     300
ttctagtcgc acgccaaaac ccggcgtgga cacgtctgca gccgacgcgg tcgtgcctgt     360
tgtaggcgga cattcctagt ttttccagga gtaactt gtg agc cag aat ggc cgt     415
                                        Val Ser Gln Asn Gly Arg
                                         1               5 ccg gta gtc ctc atc gcc gat aag ctt gcg cag tcc act gtt gac gcg       463
Pro Val Val Leu Ile Ala Asp Lys Leu Ala Gln Ser Thr Val Asp Ala
            10                  15                  20 ctt gga gat gca gta gaa gtc cgt tgg gtt gac gga cct aac cgc cca       511
Leu Gly Asp Ala Val Glu Val Arg Trp Val Asp Gly Pro Asn Arg Pro
        25                  30                  35 gaa ctg ctt gat gca gtt aag gaa gcg gac gca ctg ctc gtg cgt tct       559
Glu Leu Leu Asp Ala Val Lys Glu Ala Asp Ala Leu Leu Val Arg Ser
    40                  45                  50 gct acc act gtc gat gct gaa gtc atc gcc gct gcc cct aac ttg aag       607
Ala Thr Thr Val Asp Ala Glu Val Ile Ala Ala Ala Pro Asn Leu Lys
55                  60                  65                  70 atc gtc ggt cgt gcc ggc gtg ggc ttg gac aac gtt gac atc cct gct       655
Ile Val Gly Arg Ala Gly Val Gly Leu Asp Asn Val Asp Ile Pro Ala
                75                  80                  85 gcc act gaa gct ggc gtc atg gtt gct aac gca ccg acc tct aac att       703
Ala Thr Glu Ala Gly Val Met Val Ala Asn Ala Pro Thr Ser Asn Ile
            90                  95                 100 cac tct gct tgt gag cac gca att tct ttg ctg ctg tct act gct cgc       751
His Ser Ala Cys Glu His Ala Ile Ser Leu Leu Leu Ser Thr Ala Arg
        105                 110                 115 cag atc cct gct gct gat gcg acg ctg cgt gag ggc gag tgg aag cgg       799
Gln Ile Pro Ala Ala Asp Ala Thr Leu Arg Glu Gly Glu Trp Lys Arg
    120                 125                 130 tct tct ttc aac ggt gtg gaa att ttc gga aaa act gtc ggt atc gtc       847
Ser Ser Phe Asn Gly Val Glu Ile Phe Gly Lys Thr Val Gly Ile Val
135                 140                 145                 150 ggt ttt ggc cac att ggt cag ttg ttt gct cag cgt ctt gct gcg ttt       895
Gly Phe Gly His Ile Gly Gln Leu Phe Ala Gln Arg Leu Ala Ala Phe
                155                 160                 165 gag acc acc att gtt gct tac gat cct tac gcc aac cct gct cgt gca       943
Glu Thr Thr Ile Val Ala Tyr Asp Pro Tyr Ala Asn Pro Ala Arg Ala
            170                 175                 180 gct cag ctg aac gtt gag ttg gtt gag ttg gat gag ctg atg agc cgt       991
Ala Gln Leu Asn Val Glu Leu Val Glu Leu Asp Glu Leu Met Ser Arg
        185                 190                 195
```

```
tct gac ttt gtc acc att cac ctt cct aag acc aag gaa act gct ggc    1039
Ser Asp Phe Val Thr Ile His Leu Pro Lys Thr Lys Glu Thr Ala Gly
200                     205                     210 atg ttt gat gcg cag ctc ctt gct aag tcc aag aag ggc cag atc atc    1087
Met Phe Asp Ala Gln Leu Leu Ala Lys Ser Lys Lys Gly Gln Ile Ile
215                     220                     225             230 atc aac gct gct cgt ggt ggc ctt gtt gat gag cag gct ttg gct gat    1135
Ile Asn Ala Ala Arg Gly Gly Leu Val Asp Glu Gln Ala Leu Ala Asp
                235                     240                     245 gcg att gag tcc ggt cac att cgt ggc gct ggt ttc gat gtg tac tcc    1183
Ala Ile Glu Ser Gly His Ile Arg Gly Ala Gly Phe Asp Val Tyr Ser
            250                     255                     260 acc gag cct tgc act gat tct cct ttg ttc aag ttg cct cag gtt gtt    1231
Thr Glu Pro Cys Thr Asp Ser Pro Leu Phe Lys Leu Pro Gln Val Val
        265                     270                     275 gtg act cct cac ttg ggt gct tct act gaa gag gct cag gat cgt gcg    1279
Val Thr Pro His Leu Gly Ala Ser Thr Glu Glu Ala Gln Asp Arg Ala
    280                     285                     290 ggt act gac gtt gct gat tct gtg ctc aag gcg ctg gct ggc gag ttc    1327
Gly Thr Asp Val Ala Asp Ser Val Leu Lys Ala Leu Ala Gly Glu Phe
295                     300                     305             310 gtg gcg gat gct gtg aac gtt tcc ggt ggt cgc gtg ggc gaa gag gtt    1375
Val Ala Asp Ala Val Asn Val Ser Gly Gly Arg Val Gly Glu Glu Val
                315                     320                     325 gct gtg tgg atg gat ctg gct cgc aag ctt ggt ctt ctt gct ggc aag    1423
Ala Val Trp Met Asp Leu Ala Arg Lys Leu Gly Leu Leu Ala Gly Lys
                330                     335                     340 ctt gtc gac                                                        1432
Leu Val Asp
        345

<210> SEQ ID NO 2
<211> LENGTH: 345
<212> TYPE: PRT
<213> ORGANISM: Corynebacterium glutamicum

<400> SEQUENCE: 2

Val Ser Gln Asn Gly Arg Pro Val Val Leu Ile Ala Asp Lys Leu Ala
 1               5                  10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
```

```
                165                 170                 175
Ala Asn Pro Ala Arg Ala Ala Gln Leu Asn Val Glu Leu Val Glu Leu
                180                 185                 190
Asp Glu Leu Met Ser Arg Ser Asp Phe Val Thr Ile His Leu Pro Lys
            195                 200                 205
Thr Lys Glu Thr Ala Gly Met Phe Asp Ala Gln Leu Leu Ala Lys Ser
        210                 215                 220
Lys Lys Gly Gln Ile Ile Ile Asn Ala Ala Arg Gly Gly Leu Val Asp
225                 230                 235                 240
Glu Gln Ala Leu Ala Asp Ala Ile Glu Ser Gly His Ile Arg Gly Ala
                245                 250                 255
Gly Phe Asp Val Tyr Ser Thr Glu Pro Cys Thr Asp Ser Pro Leu Phe
            260                 265                 270
Lys Leu Pro Gln Val Val Val Thr Pro His Leu Gly Ala Ser Thr Glu
        275                 280                 285
Glu Ala Gln Asp Arg Ala Gly Thr Asp Val Ala Asp Ser Val Leu Lys
    290                 295                 300
Ala Leu Ala Gly Glu Phe Val Ala Asp Ala Val Asn Val Ser Gly Gly
305                 310                 315                 320
Arg Val Gly Glu Glu Val Ala Val Trp Met Asp Leu Ala Arg Lys Leu
                325                 330                 335
Gly Leu Leu Ala Gly Lys Leu Val Asp
                340                 345

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 3
ggacacacgt gacaaaattg tag                                        23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 4
gccagcaaga agaccaagct tgc                                        23

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 5
gtacatattg tcgttagaac gcgtaatacg actca                           35

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Primer
```

-continued

```
<400> SEQUENCE: 6
tcatcaacgc tgctcgtggt ggc                                          23

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 7
cgttagaacg cgtaatacga ctcactatag ggaga                             35

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 8
gacgttgctg attctgtgct caa                                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 9
gggagggttt agaatgtttc tag                                          23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 10
ggttcaagca aatggatctc taa                                          23

<210> SEQ ID NO 11
<211> LENGTH: 1730
<212> TYPE: DNA
<213> ORGANISM: Brevibacterium flavum
<220> FEATURE:
<221> NAME/KEY: CDS
<222> LOCATION: (115)..(1704)

<400> SEQUENCE: 11
gggagggttt agaatgtttc tagtcgcacg ccaaaacccg gcgtggacac gtctgcagcc    60
gacgcggtcg tgcctgttgt aggcggacat tcctagtttt tccaggagta actt gtg    117
                                                            Val
                                                             1 agc cag aat ggc cgt ccg gta gtc ctc atc gcc gat aag ctt gcg cag    165
Ser Gln Asn Gly Arg Pro Val Val Leu Ile Ala Asp Lys Leu Ala Gln
          5                  10                  15 tcc act gtt gac gcg ctt gga gat gca gta gaa gtc cgt tgg gtt gac    213
Ser Thr Val Asp Ala Leu Gly Asp Ala Val Glu Val Arg Trp Val Asp
        20                  25                  30 gga cct aac cgc cca gaa ctg ctt gat aca gtt aag gaa gcg gac gca    261
Gly Pro Asn Arg Pro Glu Leu Leu Asp Thr Val Lys Glu Ala Asp Ala
```

|   |   |
|---|---|
| ctg ctc gtg cgt tct gct acc act gtc gat gct gaa gtc atc gcc gct<br>Leu Leu Val Arg Ser Ala Thr Thr Val Asp Ala Glu Val Ile Ala Ala<br>50                55                      60                     65 | 309 |
| gcc cct aac ttg aag atc gtc ggt cgt gcc ggc gtg ggc ttg gac aac<br>Ala Pro Asn Leu Lys Ile Val Gly Arg Ala Gly Val Gly Leu Asp Asn<br>                    70                      75                      80 | 357 |
| gtt gac atc cct gct gcc act gaa gct ggc gtc atg gtt gct aac gca<br>Val Asp Ile Pro Ala Ala Thr Glu Ala Gly Val Met Val Ala Asn Ala<br>                        85                      90                      95 | 405 |
| ccg acc tct aac att cac tct gct tgt gag cac gca att tct ttg ctg<br>Pro Thr Ser Asn Ile His Ser Ala Cys Glu His Ala Ile Ser Leu Leu<br>            100                     105                     110 | 453 |
| ctg tct act gct cgc cag atc cct gct gct gat gcg acg ctg cgt gag<br>Leu Ser Thr Ala Arg Gln Ile Pro Ala Ala Asp Ala Thr Leu Arg Glu<br>      115                     120                     125 | 501 |
| ggc gag tgg aag cgg tct tct ttc aac ggt gtg gaa att ttc gga aaa<br>Gly Glu Trp Lys Arg Ser Ser Phe Asn Gly Val Glu Ile Phe Gly Lys<br>130                 135                     140                     145 | 549 |
| act gtc ggt atc gtc ggt ttt ggc cac att ggt cag ttg ttt gct cag<br>Thr Val Gly Ile Val Gly Phe Gly His Ile Gly Gln Leu Phe Ala Gln<br>               150                     155                     160 | 597 |
| cgt ctt gct gcg ttt gag acc acc att gtt gct tac gat cct tac gct<br>Arg Leu Ala Ala Phe Glu Thr Thr Ile Val Ala Tyr Asp Pro Tyr Ala<br>               165                     170                     175 | 645 |
| aac cct gct cgt gcg gct cag ctg aac gtt gag ttg gtt gag ttg gat<br>Asn Pro Ala Arg Ala Ala Gln Leu Asn Val Glu Leu Val Glu Leu Asp<br>          180                     185                     190 | 693 |
| gag ctg atg agc cgt tct gac ttt gtc acc att cac ctt cct aag acc<br>Glu Leu Met Ser Arg Ser Asp Phe Val Thr Ile His Leu Pro Lys Thr<br>      195                     200                     205 | 741 |
| aag gaa act gct ggc atg ttt gat gcg cag ctc ctt gct aag tcc aag<br>Lys Glu Thr Ala Gly Met Phe Asp Ala Gln Leu Leu Ala Lys Ser Lys<br>210                 215                     220                     225 | 789 |
| aag ggc cag atc atc atc aac gct gct cgt ggt ggc ctt gtt gat gaa<br>Lys Gly Gln Ile Ile Ile Asn Ala Ala Arg Gly Gly Leu Val Asp Glu<br>                    230                     235                     240 | 837 |
| cag gct ttg gct gat gcg att gag tcc ggt cac att cgt ggc gct ggt<br>Gln Ala Leu Ala Asp Ala Ile Glu Ser Gly His Ile Arg Gly Ala Gly<br>          245                     250                     255 | 885 |
| ttc gat gtg tac tcc acc gag cct tgc act gat tct cct ttg ttc aag<br>Phe Asp Val Tyr Ser Thr Glu Pro Cys Thr Asp Ser Pro Leu Phe Lys<br>               260                     265                     270 | 933 |
| ttg cct cag gtt gtt gtg act cct cac ttg ggt gct tct act gaa gag<br>Leu Pro Gln Val Val Val Thr Pro His Leu Gly Ala Ser Thr Glu Glu<br>      275                     280                     285 | 981 |
| gct cag gat cgt gcg ggt act gac gtt gct gat tct gtg ctc aag gcg<br>Ala Gln Asp Arg Ala Gly Thr Asp Val Ala Asp Ser Val Leu Lys Ala<br>290                 295                     300                     305 | 1029 |
| ctg gct ggc gag ttc gtg gcg gat gct gtg aac gtt tcc ggt ggt cgc<br>Leu Ala Gly Glu Phe Val Ala Asp Ala Val Asn Val Ser Gly Gly Arg<br>               310                     315                     320 | 1077 |
| gtg ggc gaa gag gtt gct gtg tgg atg gat ctg gct cgc aag ctt ggt<br>Val Gly Glu Glu Val Ala Val Trp Met Asp Leu Ala Arg Lys Leu Gly<br>          325                     330                     335 | 1125 |
| ctt ctt gct ggc aag ctt gtc gac gcc gcc cca gtc tcc att gag gtt<br>Leu Leu Ala Gly Lys Leu Val Asp Ala Ala Pro Val Ser Ile Glu Val<br>          340                     345                     350 | 1173 |
| gag gct cga ggc gag ctt tct tcc gag cag gtc gat gca ctt ggt ttg | 1221 |

```
Glu Ala Arg Gly Glu Leu Ser Ser Glu Gln Val Asp Ala Leu Gly Leu
            355                 360                 365 tcc gct gtt cgt ggt ttg ttc tcc gga att atc gaa gag tcc gtt act    1269
Ser Ala Val Arg Gly Leu Phe Ser Gly Ile Ile Glu Glu Ser Val Thr
370                 375                 380                 385 ttc gtc aac gct cct cgc att gct gaa gag cgt ggc ctg gac atc tcc    1317
Phe Val Asn Ala Pro Arg Ile Ala Glu Glu Arg Gly Leu Asp Ile Ser
                390                 395                 400 gtg aag acc aac tct gag tct gtt act cac cgt tcc gtc ctg cag gtc    1365
Val Lys Thr Asn Ser Glu Ser Val Thr His Arg Ser Val Leu Gln Val
            405                 410                 415 aag gtc att act ggc agc ggc gcg agc gca act gtt gtt ggt gcc ctg    1413
Lys Val Ile Thr Gly Ser Gly Ala Ser Ala Thr Val Val Gly Ala Leu
        420                 425                 430 act ggt ctt gag cgc gtt gag aag atc acc cgc atc aat ggc cgt ggc    1461
Thr Gly Leu Glu Arg Val Glu Lys Ile Thr Arg Ile Asn Gly Arg Gly
    435                 440                 445 ctg gat ctg cgc gca gag ggt ctg aac ctc ttc ctg cag tac act gac    1509
Leu Asp Leu Arg Ala Glu Gly Leu Asn Leu Phe Leu Gln Tyr Thr Asp
450                 455                 460                 465 gct cct ggt gca ctg ggt acc gtt ggt acc aag ctg ggt gct gct ggc    1557
Ala Pro Gly Ala Leu Gly Thr Val Gly Thr Lys Leu Gly Ala Ala Gly
                470                 475                 480 atc aac atc gag gct gct gcg ttg act cag gct gag aag ggt gac ggc    1605
Ile Asn Ile Glu Ala Ala Ala Leu Thr Gln Ala Glu Lys Gly Asp Gly
            485                 490                 495 gct gtc ctg atc ctg cgt gtt gag tcc gct gtc tcc gaa gag ctg gaa    1653
Ala Val Leu Ile Leu Arg Val Glu Ser Ala Val Ser Glu Glu Leu Glu
        500                 505                 510 gct gaa atc aac gct gag ttg ggt gct act tcc ttc cag gtt gat ctt    1701
Ala Glu Ile Asn Ala Glu Leu Gly Ala Thr Ser Phe Gln Val Asp Leu
    515                 520                 525 gac taattagaga tccattttct agaacc                                    1730
Asp
530

<210> SEQ ID NO 12
<211> LENGTH: 530
<212> TYPE: PRT
<213> ORGANISM: Brevibacterium flavum

<400> SEQUENCE: 12

Val Ser Gln Asn Gly Arg Pro Val Val Leu Ile Ala Asp Lys Leu Ala
  1               5                  10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Thr Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125
```

```
Glu Gly Glu Trp Lys Arg Ser Ser Phe Asn Gly Val Glu Ile Phe Gly
        130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
            195                 200                 205

Thr Lys Glu Thr Ala Gly Met Phe Asp Ala Gln Leu Leu Ala Lys Ser
        210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270

Lys Leu Pro Gln Val Val Thr Pro His Leu Gly Ala Ser Thr Glu
            275                 280                 285

Glu Ala Gln Asp Arg Ala Gly Thr Asp Val Ala Asp Ser Val Leu Lys
        290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala Arg Lys Leu
                325                 330                 335

Gly Leu Leu Ala Gly Lys Leu Val Asp Ala Ala Pro Val Ser Ile Glu
            340                 345                 350

Val Glu Ala Arg Gly Glu Leu Ser Ser Glu Gln Val Asp Ala Leu Gly
        355                 360                 365

Leu Ser Ala Val Arg Gly Leu Phe Ser Gly Ile Ile Glu Glu Ser Val
    370                 375                 380

Thr Phe Val Asn Ala Pro Arg Ile Ala Glu Glu Arg Gly Leu Asp Ile
385                 390                 395                 400

Ser Val Lys Thr Asn Ser Glu Ser Val Thr His Arg Ser Val Leu Gln
                405                 410                 415

Val Lys Val Ile Thr Gly Ser Gly Ala Ser Ala Thr Val Gly Ala
            420                 425                 430

Leu Thr Gly Leu Glu Arg Val Glu Lys Ile Thr Arg Ile Asn Gly Arg
        435                 440                 445

Gly Leu Asp Leu Arg Ala Glu Gly Leu Asn Leu Phe Leu Gln Tyr Thr
    450                 455                 460

Asp Ala Pro Gly Ala Leu Gly Thr Val Gly Thr Lys Leu Gly Ala Ala
465                 470                 475                 480

Gly Ile Asn Ile Glu Ala Ala Ala Leu Thr Gln Ala Glu Lys Gly Asp
                485                 490                 495

Gly Ala Val Leu Ile Leu Arg Val Glu Ser Ala Val Ser Glu Glu Leu
            500                 505                 510

Glu Ala Glu Ile Asn Ala Glu Leu Gly Ala Thr Ser Phe Gln Val Asp
        515                 520                 525

Leu Asp
    530
```

```
<210> SEQ ID NO 13
<211> LENGTH: 1730
<212> TYPE: DNA
<213> ORGANISM: Brevibacterium flavum
<220> FEATURE:
<221> NAME/KEY: CDS
<222> LOCATION: (115)..(1704)

<400> SEQUENCE: 13
gggagggttt agaatgtttc tagtcgcacg ccaaaacccg gcgtggacac gtctgcagcc      60
gacgcggtcg tgcctgttgt aggcggacat tcctagtttt tccaggagta actt gtg     117
                                                          Val
                                                            1 agc cag aat ggc cgt ccg gta gtc ctc atc gcc gat aag ctt gcg cag     165
Ser Gln Asn Gly Arg Pro Val Val Leu Ile Ala Asp Lys Leu Ala Gln
          5                  10                  15 tcc act gtt gac gcg ctt gga gat gca gta gaa gtc cgt tgg gtt gac     213
Ser Thr Val Asp Ala Leu Gly Asp Ala Val Glu Val Arg Trp Val Asp
     20                  25                  30 gga cct aac cgc cca gaa ctg ctt gat aca gtt aag gaa gcg gac gca     261
Gly Pro Asn Arg Pro Glu Leu Leu Asp Thr Val Lys Glu Ala Asp Ala
 35                  40                  45 ctg ctc gtg cgt tct gct acc act gtc gat gct gaa gtc atc gcc gct     309
Leu Leu Val Arg Ser Ala Thr Thr Val Asp Ala Glu Val Ile Ala Ala
 50                  55                  60                  65 gcc cct aac ttg aag atc gtc ggt cgt gcc ggc gtg ggc ttg gac aac     357
Ala Pro Asn Leu Lys Ile Val Gly Arg Ala Gly Val Gly Leu Asp Asn
                 70                  75                  80 gtt gac atc cct gct gcc act gaa gct ggc gtc atg gtt gct aac gca     405
Val Asp Ile Pro Ala Ala Thr Glu Ala Gly Val Met Val Ala Asn Ala
             85                  90                  95 ccg acc tct aac att cac tct gct tgt gag cac gca att tct ttg ctg     453
Pro Thr Ser Asn Ile His Ser Ala Cys Glu His Ala Ile Ser Leu Leu
        100                 105                 110 ctg tct act gct cgc cag atc cct gct gct gat gcg acg ctg cgt gag     501
Leu Ser Thr Ala Arg Gln Ile Pro Ala Ala Asp Ala Thr Leu Arg Glu
    115                 120                 125 ggc gag tgg aag cgg tct tct ttc aac ggt gtg gaa att ttc gga aaa     549
Gly Glu Trp Lys Arg Ser Ser Phe Asn Gly Val Glu Ile Phe Gly Lys
130                 135                 140                 145 act gtc ggt atc gtc ggt ttt ggc cac att ggt cag ttg ttt gct cag     597
Thr Val Gly Ile Val Gly Phe Gly His Ile Gly Gln Leu Phe Ala Gln
                150                 155                 160 cgt ctt gct gcg ttt gag acc acc att gtt gct tac gat cct tac gct     645
Arg Leu Ala Ala Phe Glu Thr Thr Ile Val Ala Tyr Asp Pro Tyr Ala
            165                 170                 175 aac cct gct cgt gcg gct cag ctg aac gtt gag ttg gtt gag ttg gat     693
Asn Pro Ala Arg Ala Ala Gln Leu Asn Val Glu Leu Val Glu Leu Asp
        180                 185                 190 gag ctg atg agc cgt tct gac ttt gtc acc att cac ctt cct aag acc     741
Glu Leu Met Ser Arg Ser Asp Phe Val Thr Ile His Leu Pro Lys Thr
    195                 200                 205 aag gaa act gct ggc atg ttt gat gcg cag ctc ctt gct aag tcc aag     789
Lys Glu Thr Ala Gly Met Phe Asp Ala Gln Leu Leu Ala Lys Ser Lys
210                 215                 220                 225 aag ggc cag atc atc atc aac gct gct cgt ggt ggc ctt gtt gat gaa     837
Lys Gly Gln Ile Ile Ile Asn Ala Ala Arg Gly Gly Leu Val Asp Glu
                230                 235                 240 cag gct ttg gct gat gcg att gag tcc ggt cac att cgt ggc gct ggt     885
Gln Ala Leu Ala Asp Ala Ile Glu Ser Gly His Ile Arg Gly Ala Gly
            245                 250                 255
```

```
ttc gat gtg tac tcc acc gag cct tgc act gat tct cct ttg ttc aag      933
Phe Asp Val Tyr Ser Thr Glu Pro Cys Thr Asp Ser Pro Leu Phe Lys
        260                 265                 270 ttg cct cag gtt gtt gtg act cct cac ttg ggt gct tct act gaa gag      981
Leu Pro Gln Val Val Val Thr Pro His Leu Gly Ala Ser Thr Glu Glu
    275                 280                 285 gct cag gat cgt gcg ggt act gac gtt gct gat tct gtg ctc aag gcg     1029
Ala Gln Asp Arg Ala Gly Thr Asp Val Ala Asp Ser Val Leu Lys Ala
290                 295                 300                 305 ctg gct ggc gag ttc gtg gcg gat gct gtg aac gtt tcc ggt ggt cgc     1077
Leu Ala Gly Glu Phe Val Ala Asp Ala Val Asn Val Ser Gly Gly Arg
                310                 315                 320 gtg ggc gaa aag gtt gct gtg tgg atg gat ctg gct cgc aag ctt ggt     1125
Val Gly Glu Lys Val Ala Val Trp Met Asp Leu Ala Arg Lys Leu Gly
            325                 330                 335 ctt ctt gct ggc aag ctt gtc gac gcc gcc cca gtc tcc att gag gtt     1173
Leu Leu Ala Gly Lys Leu Val Asp Ala Ala Pro Val Ser Ile Glu Val
        340                 345                 350 gag gct cga ggc gag ctt tct tcc gag cag gtc gat gca ctt ggt ttg     1221
Glu Ala Arg Gly Glu Leu Ser Ser Glu Gln Val Asp Ala Leu Gly Leu
    355                 360                 365 tcc gct gtt cgt ggt ttg ttc tcc gga att atc gaa gag tcc gtt act     1269
Ser Ala Val Arg Gly Leu Phe Ser Gly Ile Ile Glu Glu Ser Val Thr
370                 375                 380                 385 ttc gtc aac gct cct cgc att gct gaa gag cgt ggc ctg gac atc tcc     1317
Phe Val Asn Ala Pro Arg Ile Ala Glu Glu Arg Gly Leu Asp Ile Ser
                390                 395                 400 gtg aag acc aac tct gag tct gtt act cac cgt tcc gtc ctg cag gtc     1365
Val Lys Thr Asn Ser Glu Ser Val Thr His Arg Ser Val Leu Gln Val
            405                 410                 415 aag gtc att act ggc agc ggc gcg agc gca act gtt gtt ggt gcc ctg     1413
Lys Val Ile Thr Gly Ser Gly Ala Ser Ala Thr Val Val Gly Ala Leu
        420                 425                 430 act ggt ctt gag cgc gtt gag aag atc acc cgc atc aat ggc cgt ggc     1461
Thr Gly Leu Glu Arg Val Glu Lys Ile Thr Arg Ile Asn Gly Arg Gly
    435                 440                 445 ctg gat ctg cgc gca gag ggt ctg aac ctc ttc ctg cag tac act gac     1509
Leu Asp Leu Arg Ala Glu Gly Leu Asn Leu Phe Leu Gln Tyr Thr Asp
450                 455                 460                 465 gct cct ggt gca ctg ggt acc gtt ggt acc aag ctg ggt gct gct ggc     1557
Ala Pro Gly Ala Leu Gly Thr Val Gly Thr Lys Leu Gly Ala Ala Gly
                470                 475                 480 atc aac atc gag gct gct gcg ttg act cag gct gag aag ggt gac ggc     1605
Ile Asn Ile Glu Ala Ala Ala Leu Thr Gln Ala Glu Lys Gly Asp Gly
            485                 490                 495 gct gtc ctg atc ctg cgt gtt gag tcc gct gtc tcc gaa gag ctg gaa     1653
Ala Val Leu Ile Leu Arg Val Glu Ser Ala Val Ser Glu Glu Leu Glu
        500                 505                 510 gct gaa atc aac gct gag ttg ggt gct act tcc ttc cag gtt gat ctt     1701
Ala Glu Ile Asn Ala Glu Leu Gly Ala Thr Ser Phe Gln Val Asp Leu
    515                 520                 525 gac taattagaga tccattttct agaacc                                    1730
Asp
530

<210> SEQ ID NO 14
<211> LENGTH: 530
<212> TYPE: PRT
<213> ORGANISM: Brevibacterium flavum
```

<400> SEQUENCE: 14

```
Val Ser Gln Asn Gly Arg Pro Val Leu Ile Ala Asp Lys Leu Ala
  1               5                  10                  15

Gln Ser Thr Val Asp Ala Leu Gly Asp Ala Val Glu Val Arg Trp Val
                 20                  25                  30

Asp Gly Pro Asn Arg Pro Glu Leu Leu Asp Thr Val Lys Glu Ala Asp
             35                  40                  45

Ala Leu Leu Val Arg Ser Ala Thr Thr Val Asp Ala Glu Val Ile Ala
         50                  55                  60

Ala Ala Pro Asn Leu Lys Ile Val Gly Arg Ala Gly Val Gly Leu Asp
 65                  70                  75                  80

Asn Val Asp Ile Pro Ala Ala Thr Glu Ala Gly Val Met Val Ala Asn
                 85                  90                  95

Ala Pro Thr Ser Asn Ile His Ser Ala Cys Glu His Ala Ile Ser Leu
                100                 105                 110

Leu Leu Ser Thr Ala Arg Gln Ile Pro Ala Ala Asp Ala Thr Leu Arg
            115                 120                 125

Glu Gly Glu Trp Lys Arg Ser Ser Phe Asn Gly Val Glu Ile Phe Gly
130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
                180                 185                 190

Asp Glu Leu Met Ser Arg Ser Asp Phe Val Thr Ile His Leu Pro Lys
            195                 200                 205

Thr Lys Glu Thr Ala Gly Met Phe Asp Ala Gln Leu Leu Ala Lys Ser
210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
                260                 265                 270

Lys Leu Pro Gln Val Val Thr Pro His Leu Gly Ala Ser Thr Glu
            275                 280                 285

Glu Ala Gln Asp Arg Ala Gly Thr Asp Val Ala Asp Ser Val Leu Lys
290                 295                 300

Ala Leu Ala Gly Glu Phe Val Ala Asp Ala Val Asn Val Ser Gly Gly
305                 310                 315                 320

Arg Val Gly Glu Lys Val Ala Val Trp Met Asp Leu Ala Arg Lys Leu
                325                 330                 335

Gly Leu Leu Ala Gly Lys Leu Val Asp Ala Ala Pro Val Ser Ile Glu
            340                 345                 350

Val Glu Ala Arg Gly Glu Leu Ser Glu Gln Val Asp Ala Leu Gly
            355                 360                 365

Leu Ser Ala Val Arg Gly Leu Phe Ser Gly Ile Ile Glu Glu Ser Val
370                 375                 380

Thr Phe Val Asn Ala Pro Arg Ile Ala Glu Glu Arg Gly Leu Asp Ile
385                 390                 395                 400

Ser Val Lys Thr Asn Ser Glu Ser Val Thr His Arg Ser Val Leu Gln
                405                 410                 415
```

-continued

```
Val Lys Val Ile Thr Gly Ser Gly Ala Ser Ala Thr Val Val Gly Ala
            420                 425                 430

Leu Thr Gly Leu Glu Arg Val Glu Lys Ile Thr Arg Ile Asn Gly Arg
        435                 440                 445

Gly Leu Asp Leu Arg Ala Glu Gly Leu Asn Leu Phe Leu Gln Tyr Thr
        450                 455                 460

Asp Ala Pro Gly Ala Leu Gly Thr Val Gly Thr Lys Leu Gly Ala Ala
465                     470                 475                 480

Gly Ile Asn Ile Glu Ala Ala Ala Leu Thr Gln Ala Glu Lys Gly Asp
                485                 490                 495

Gly Ala Val Leu Ile Leu Arg Val Glu Ser Ala Val Ser Glu Glu Leu
            500                 505                 510

Glu Ala Glu Ile Asn Ala Glu Leu Gly Ala Thr Ser Phe Gln Val Asp
        515                 520                 525

Leu Asp
    530
```